(12) United States Patent
Renke

(10) Patent No.: US 10,070,951 B2
(45) Date of Patent: Sep. 11, 2018

(54) ADJUSTABLE IMPLANT WITH SELF-SEALING ELASTOMERIC MEMBRANE AND METHODS OF FABRICATION THEREOF

(71) Applicant: ImplantAdjust LLC, Point Roberts, WA (US)

(72) Inventor: Peter Renke, Vancouver (CA)

(73) Assignee: ImplantAdjust, LLC, Point Roberts, WA (US)

( * ) Notice: Subject to any disclaimer, the term of this patent is extended or adjusted under 35 U.S.C. 154(b) by 0 days.

(21) Appl. No.: 15/133,651

(22) Filed: Apr. 20, 2016

(65) Prior Publication Data

US 2016/0228237 A1    Aug. 11, 2016

Related U.S. Application Data

(62) Division of application No. 14/079,180, filed on Nov. 13, 2013, now Pat. No. 9,351,824.

(Continued)

(51) Int. Cl.
*B29C 41/50* (2006.01)
*A61F 2/12* (2006.01)
(Continued)

(52) U.S. Cl.
CPC ............ *A61F 2/12* (2013.01); *B29C 35/0266* (2013.01); *B29C 41/08* (2013.01); *B29C 41/22* (2013.01); *B29C 41/50* (2013.01); *B29C 61/006* (2013.01); *B29C 73/20* (2013.01); *B32B 1/00* (2013.01); *B32B 3/266* (2013.01); *B32B 27/08* (2013.01); *B32B 27/20* (2013.01); *B32B 27/283* (2013.01); *A61F 2240/001* (2013.01); *B29K 2021/00* (2013.01); *B29K 2105/0058* (2013.01); *B29K 2805/00* (2013.01); *B29K 2909/00* (2013.01); *B29K 2995/0046* (2013.01); *B29K 2995/0069* (2013.01); *B29L 2031/7532* (2013.01); *B32B 2250/03* (2013.01); *B32B 2307/51* (2013.01);
(Continued)

(58) Field of Classification Search
None
See application file for complete search history.

(56) References Cited

U.S. PATENT DOCUMENTS 3,919,724 A    11/1975    Sanders et al.
4,428,364 A    1/1984    Bartolo
(Continued)

FOREIGN PATENT DOCUMENTS

CA    1121553 A1    4/1982
EP    0134340 B1    11/1988
(Continued)

*Primary Examiner* — Monica A Huson
(74) *Attorney, Agent, or Firm* — The Webb Law Firm

(57) ABSTRACT

A method of forming a fluid-filled implant is provided. The method includes: forming a first zone of an elastomeric membrane defining at least one partially enclosed void space; expanding a volume of the void space, thereby expanding a volume enclosed by the first zone; forming a second zone comprising at least one elastomeric middle layer on at least a portion of the expanded first zone; and reducing the volume of the void space, thereby contracting elastomeric layers of the first zone and the second zone. The method also includes forming an adjustable implant from the elastomeric membrane by enclosing the void space to form at least one chamber.

20 Claims, 6 Drawing Sheets

Related U.S. Application Data

(60) Provisional application No. 61/726,198, filed on Nov. 14, 2012.

(51) Int. Cl.

| | | |
|---|---|---|
| *B29C 35/02* | (2006.01) | |
| *B29C 41/22* | (2006.01) | |
| *B29C 41/08* | (2006.01) | |
| *B32B 27/08* | (2006.01) | |
| *B32B 27/20* | (2006.01) | |
| *B32B 27/28* | (2006.01) | |
| *B32B 1/00* | (2006.01) | |
| *B32B 3/26* | (2006.01) | |
| *B29C 73/20* | (2006.01) | |
| *B29C 61/00* | (2006.01) | |
| *B29L 31/00* | (2006.01) | |
| *B29K 21/00* | (2006.01) | |
| *B29K 105/00* | (2006.01) | |

(52) U.S. Cl.
 CPC ... *B32B 2307/7265* (2013.01); *B32B 2535/00* (2013.01)

(56) References Cited

U.S. PATENT DOCUMENTS

| | | |
|---|---|---|
| 4,636,213 A | 1/1987 | Pakiam |
| 4,650,487 A | 3/1987 | Chaglassian |
| 4,671,255 A | 6/1987 | Dubrul et al. |
| 4,685,447 A | 8/1987 | Iversen et al. |
| 4,738,657 A | 4/1988 | Hancock et al. |
| 4,798,584 A | 1/1989 | Hancock et al. |
| 4,944,749 A | 7/1990 | Becker |
| 5,066,303 A | 11/1991 | Bark et al. |
| 5,282,857 A | 2/1994 | Perry et al. |
| 5,376,323 A | 12/1994 | Eaton |
| 5,383,929 A | 1/1995 | Ledergerber |
| 5,447,535 A | 9/1995 | Muller |
| 5,496,367 A | 3/1996 | Fisher |
| 5,525,275 A | 6/1996 | Iversen et al. |
| 5,545,221 A | 8/1996 | Hang-Fu |
| 5,571,179 A | 11/1996 | Manders et al. |
| 5,630,844 A | 5/1997 | Dogan et al. |
| 5,662,708 A | 9/1997 | Hayes et al. |
| 5,683,420 A | 11/1997 | Jeter et al. |
| 5,695,338 A | 12/1997 | Robert |
| 5,803,746 A | 9/1998 | Barrie et al. |
| 5,935,164 A | 8/1999 | Iversen |
| 6,060,639 A | 5/2000 | Petrick |
| 6,156,065 A | 12/2000 | Eaton |
| 6,187,043 B1 | 2/2001 | Ledergerber |
| 6,315,796 B1 | 11/2001 | Eaton |
| 6,743,254 B2 | 6/2004 | Guest et al. |
| 6,755,861 B2 | 6/2004 | Nakao |
| 6,780,366 B2 | 8/2004 | Vang et al. |
| 6,783,546 B2 | 8/2004 | Zucherman et al. |
| 6,802,861 B1 | 10/2004 | Hamas |
| 7,081,136 B1 | 7/2006 | Becker |
| 7,226,463 B2 | 6/2007 | Gedebou |
| 7,364,540 B1 | 4/2008 | Burton et al. |
| 7,731,700 B1 | 6/2010 | Schytte |
| 8,070,674 B1 | 12/2011 | Hughes |
| 8,349,007 B2 | 1/2013 | Berg et al. |
| 8,377,127 B2 | 2/2013 | Schuessler |
| 8,398,710 B2 | 3/2013 | Forsell |
| 8,431,179 B2 | 4/2013 | Judge et al. |
| 2002/0151763 A1 | 10/2002 | Cook et al. |
| 2005/0283119 A1 | 12/2005 | Uth et al. |
| 2006/0224239 A1 | 10/2006 | Tiahrt |
| 2006/0281964 A1 | 12/2006 | Burton et al. |
| 2007/0050027 A1 | 3/2007 | McGhan et al. |
| 2007/0233273 A1 | 10/2007 | Connell |
| 2010/0049316 A1 | 2/2010 | Schuessler |
| 2010/0114311 A1 | 5/2010 | Becker |
| 2010/0204792 A1 | 8/2010 | Greco |
| 2011/0270391 A1 | 11/2011 | Chitre et al. |
| 2012/0078284 A1 | 3/2012 | Jones et al. |
| 2012/0123537 A1 | 5/2012 | Manesis et al. |
| 2012/0277524 A1 | 11/2012 | Franklin et al. |
| 2013/0116784 A1 | 5/2013 | Hamas et al. |
| 2013/0131799 A1 | 5/2013 | Schuessler |

FOREIGN PATENT DOCUMENTS

| | | |
|---|---|---|
| EP | 0181720 B1 | 5/1990 |
| EP | 0412703 A1 | 2/1991 |
| EP | 0422302 B1 | 9/1993 |
| EP | 0996389 B1 | 5/2000 |
| EP | 1189552 B1 | 3/2002 |
| EP | 1229857 B1 | 8/2002 |
| EP | 1736196 B2 | 8/2008 |
| EP | 1736199 B1 | 2/2009 |
| EP | 1736202 B1 | 7/2009 |
| EP | 1815881 B1 | 11/2009 |
| EP | 2554138 A1 | 2/2013 |
| FR | 2953122 A1 | 6/2011 |
| GB | 2151927 A | 7/1985 |
| JP | 03140155 A | 6/1991 |
| WO | 9705832 A1 | 2/1997 |
| WO | 9856311 A1 | 12/1998 |
| WO | 0066030 A1 | 11/2000 |
| WO | 0069374 A1 | 11/2000 |
| WO | 0126581 A1 | 4/2001 |
| WO | 0152774 A1 | 7/2001 |
| WO | 03065940 A1 | 8/2003 |
| WO | 2004066812 A2 | 8/2004 |
| WO | 2004112656 A2 | 12/2004 |
| WO | 2009129474 A1 | 10/2009 |
| WO | 2010022131 A1 | 2/2010 |
| WO | 2011058550 A1 | 5/2011 |
| WO | 2011097292 A1 | 8/2011 |
| WO | 2011097451 A1 | 8/2011 |
| WO | 2012064683 A1 | 5/2012 |
| WO | 2012154948 A1 | 11/2012 |
| WO | 2012154952 A1 | 11/2012 |
| WO | 2013058878 A1 | 4/2013 |

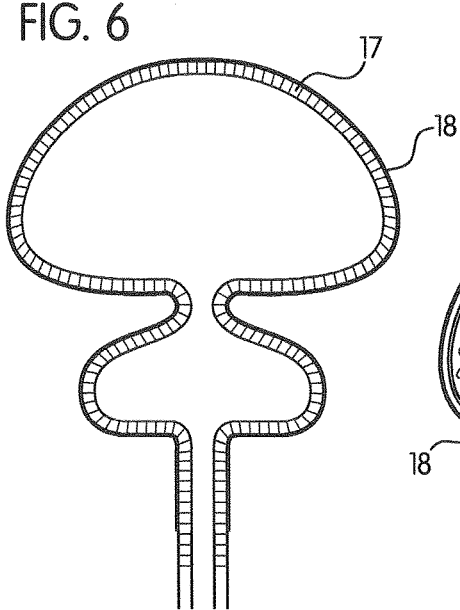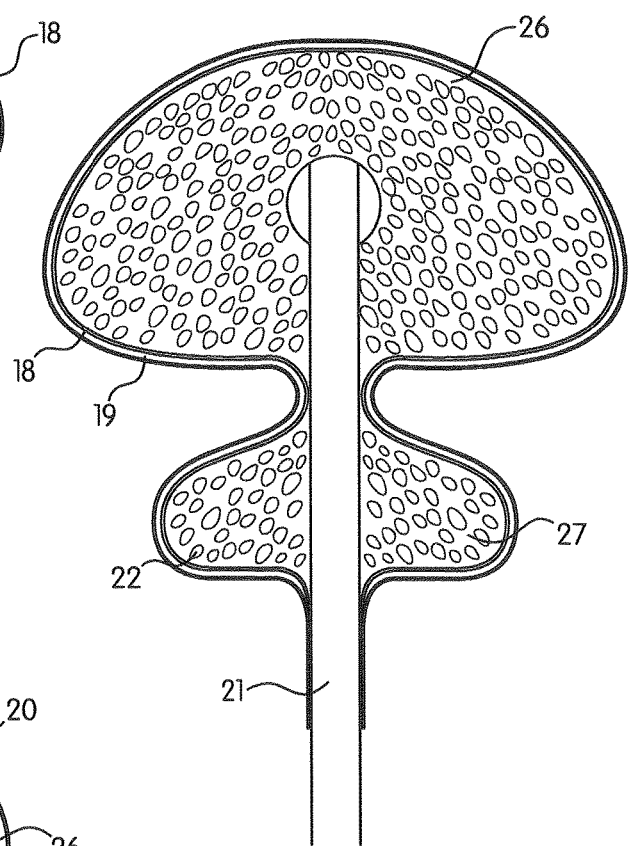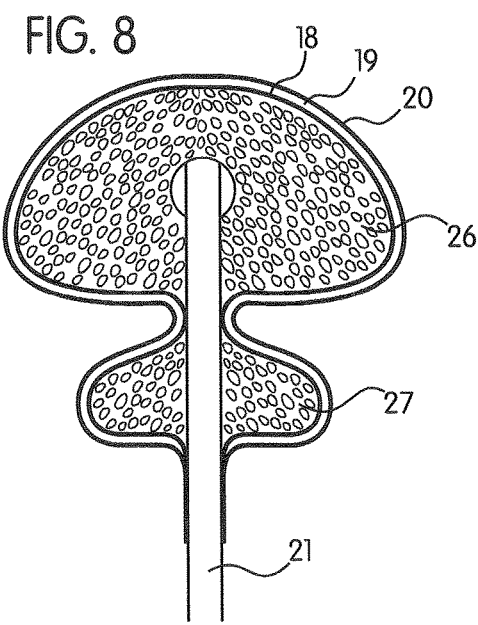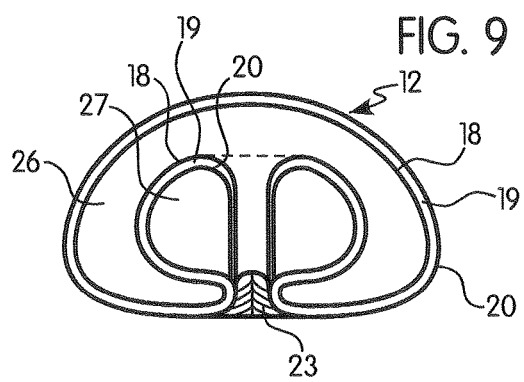

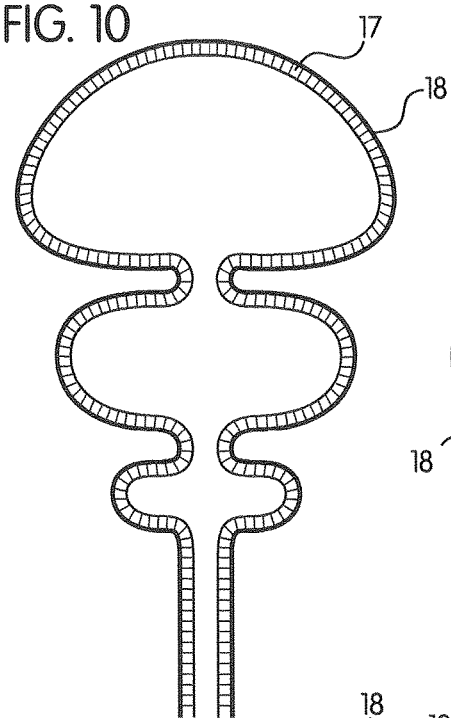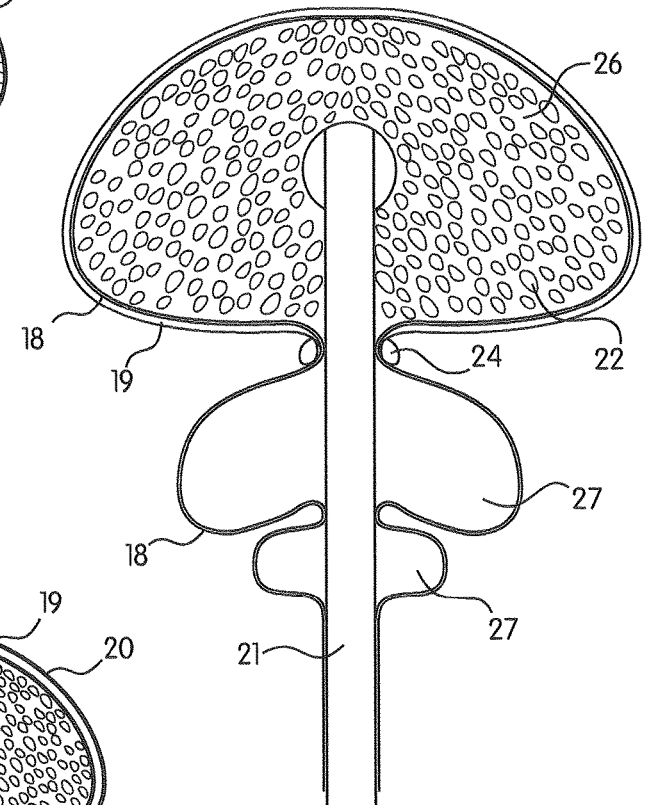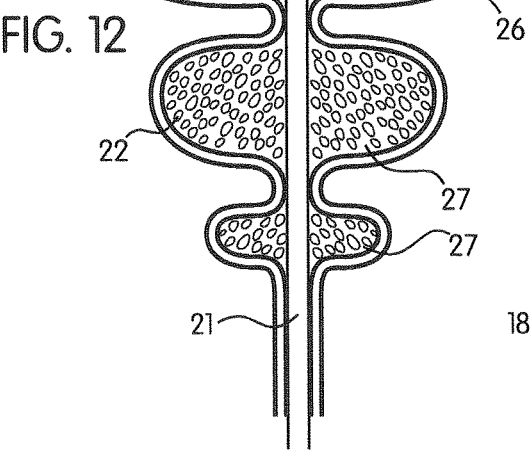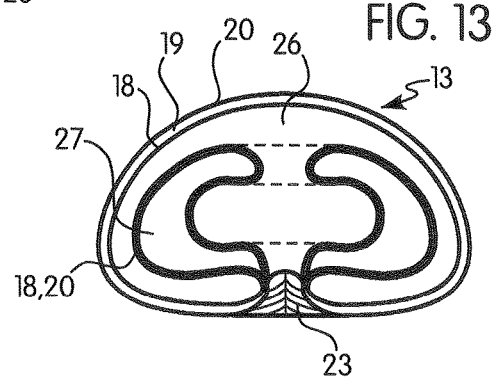

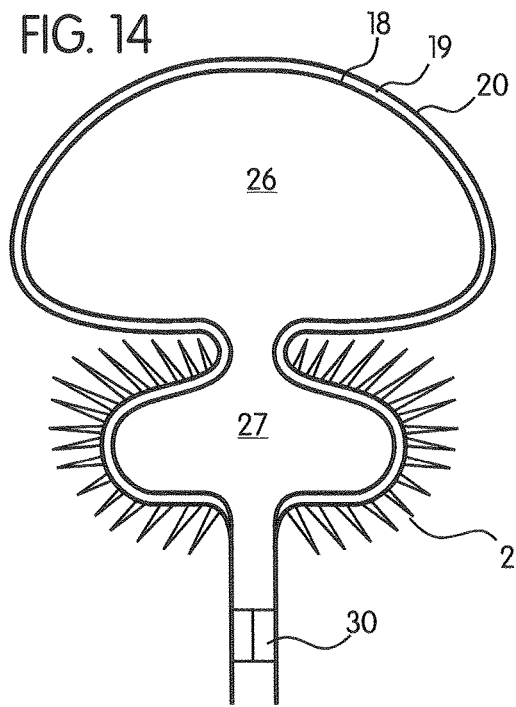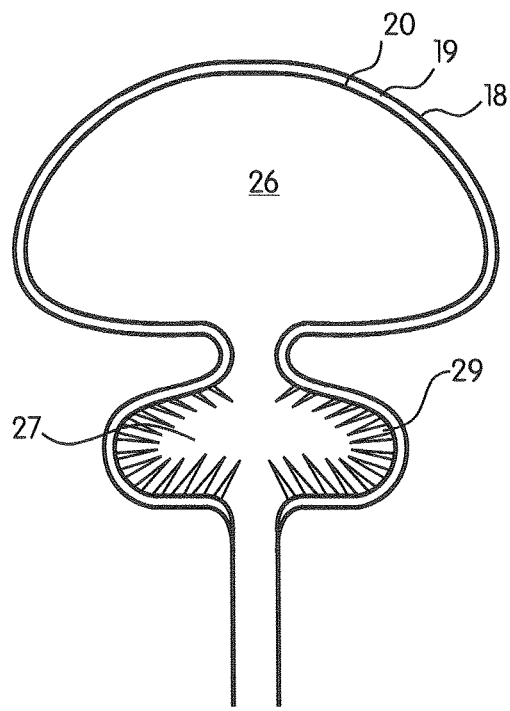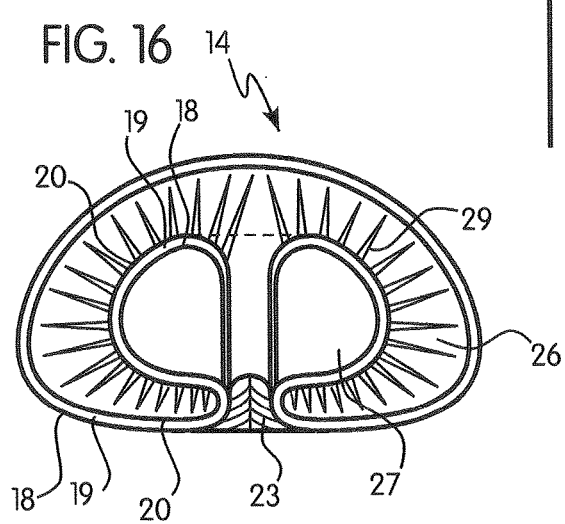

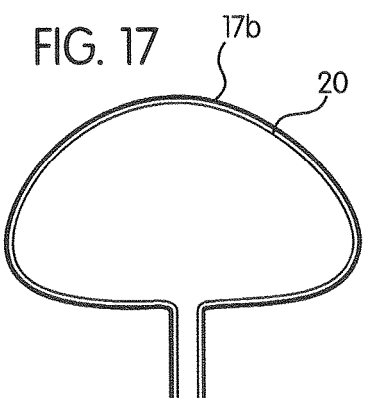
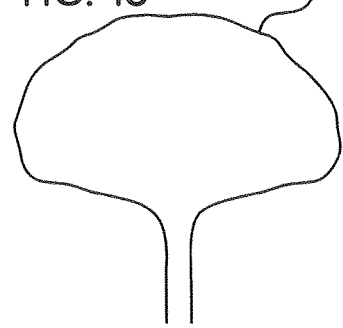
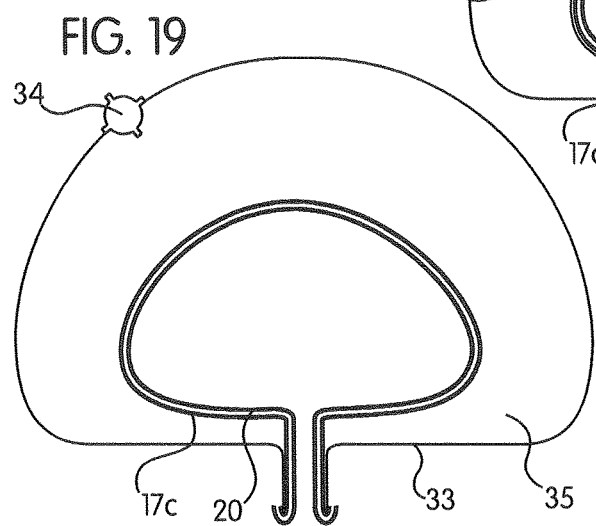
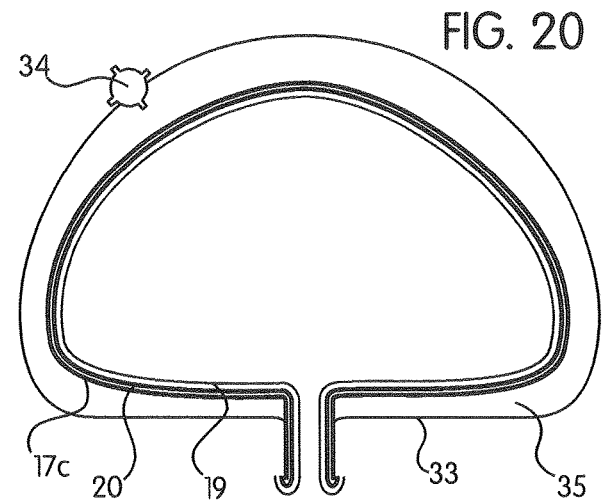
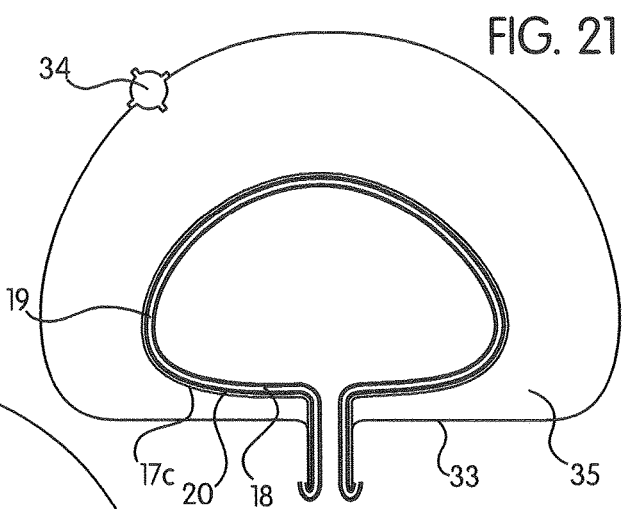
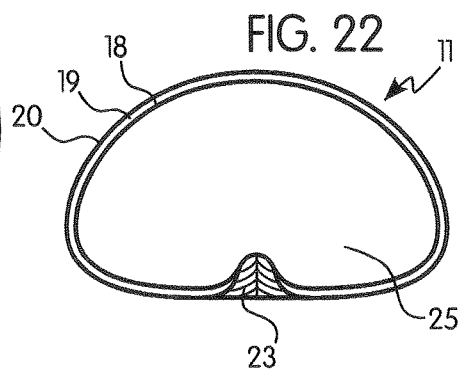

US 10,070,951 B2

ADJUSTABLE IMPLANT WITH SELF-SEALING ELASTOMERIC MEMBRANE AND METHODS OF FABRICATION THEREOF

CROSS REFERENCE TO RELATED APPLICATIONS

This application is a divisional of U.S. patent application Ser. No. 14/079,180 filed Nov. 13, 2013, which claims priority to U.S. Provisional Patent Application No. 61/726,198 filed on Nov. 14, 2012, each of which is hereby incorporated by reference in its entirety.

BACKGROUND OF THE INVENTION

Field of the Invention

This invention generally relates to fluid-filled inflatable chambered prosthetic implants and methods of fabrication thereof, which are employed to volumetrically alter, replace, expand, or augment tissues, and, more particularly, to adjustable implants formed from self-sealing elastomeric membranes.

Description of Related Art

Breast reconstruction after mastectomy presents challenges as a result of tissue loss and scarring. The tight chest-wall skin can often require skin grafting to replace lost tissue. Expanding the skin is a more desirable method to avoid skin grafting. Temporary skin expanders can be utilized but require eventual removal and replacement with the appropriate permanent implant. The multiple surgical procedures are difficult for the patient and introduce additional risks and costs. This invention will make a single surgery possible with slow expansion of the tissues remaining after the mastectomy. The implant can potentially be adjusted at any time, even years after the initial surgery.

Many breast implants are commercially available. A single chamber design is most common, and is available in a variety of fixed volumes to produce a range of sizes and shape characteristics from about 80 to 800 cubic centimeters. As used herein, "chamber" refers to the interior portion of a breast implant, which is enclosed by an outer shell or membrane. As is known by those skilled in the art, the interior portion of an implant may also be referred to as a lumen. The implants are generally filled with silicone gel or saline. Viscoelastic silicone shells of all implants are very similar in composition, but vary in thickness, texture, and surface treatments. There are very significant differences with respect to the filling materials. The silicone gel implants generally have more natural properties, with fewer noticeable edges and rippling effects. The viscosity of the silicone gel reduces fluid motion that results in these beneficial properties. The silicone gel filling the implant may alter over time to become firmer, softer, and change in elasticity, depending on its composition. Historically, a major complication has been gel bleed leading to capsular contraction and tissue toxicity to the patient. Many gel-filled implants have additional barrier coatings or layers to lessen the diffusion of silicone into the tissues. Diffusion can be reduced, but not eliminated.

Saline implants were developed to eliminate complications related to fluid bleed. Saline is biocompatible and able to be absorbed without tissue toxicity complications in the event of a slow bleed or rupture of the implant. The low viscosity of saline allows for significant fluid motion leading to deformation of the fluid-filled shell. The wave and ripple motion is often visible through the overlying tissue. This is a more significant complication in cases where there are not significant amounts of tissue surrounding the implant. The deformation of the viscoelastic membrane can cause the surrounding tissue to scar and contract, distorting and hardening the feel of the implant. Saline implants are often placed deep under muscle tissue of the chest and slightly overfilled to prevent complications.

Shell coatings and texturing have been developed to reduce capsular contraction, with reasonable success. The variable surface treatments all work by enabling tissues to adhere and distribute forces responsible for contracture. The materials utilized to form, coat, and fill the implants have resulted in a wide variety of available designs. Size and shape alone produce many options. The designs become more involved when multi-chamber and variable volumetric designs are considered. Variability of volume during surgery allows for adjustments to be made for general size and symmetry. Access ports and valves are used to inflate or deflate the implant. In some cases, the filling tube is left in place for a short period to allow for further adjustments post-surgery. This adjustability is a desirable and, often, a necessary feature in the case of tissue expanders.

Multi-chamber implants predominantly consist of an inner chamber and an outer chamber filled with silicone, saline, or a combination of both. The combination of chambers allows for greater variability in size and shape characteristics. Currently available models have a double membrane, double chamber design, in which an outer chamber has a fixed volume of gel and an adjustable inner chamber is filled with saline. These implants provide a very natural appearance and feel with the added advantage of temporary adjustability. These more complex designs have been found to be less resistant to shear forces in areas where there are junctions between the membranes and valve port.

Implants are intended to safely provide a natural feel and appearance, while minimizing leakage and contracture. Therefore, there is a need for an implant that achieves necessary performance and safety. It would also be beneficial for the implant to remain adjustable following surgery, to allow for appropriate correction if the patient physically changes or has different expectations after the surgery is completed. Such adjustments must be performed in a safe manner, without increasing risk to the patient or requiring additional surgical procedures. The implant should also be configured to adjust for minor leakages over time. The implants and methods of formation thereof provided herein address some or all of these needs.

SUMMARY OF THE INVENTION

The present invention is of particular use in relation to breast reconstruction and augmentation, but is not limited to this field. For purposes of illustration and description, breast implants will be utilized as exemplary of the invention. Variations of the invention can be utilized for tissue volume replacement and as a tissue expanding device to form tissues in post-traumatic surgery or in advance of planned surgery to prepare tissue flaps. As such, the invention can be employed as a permanent prosthesis or temporary device, as indicated. Methods of manufacture make custom forms of this invention possible at an accessible cost. As such, this invention can be employed in planned, highly invasive surgeries, such as large tumor removal. An implant can be fabricated in advance to replace the desired volume and form of tissues removed. As such, the implant can be utilized to slowly be expanded or contracted over time to achieve the desired shape allowing tissues to slowly conform in a safe and predictable manner.

In general, the invention provides for an implant consisting of a continuous, preferably self-sealing, elastomeric membrane design that can be configured to produce a variety of implant options. By nature of its design, the membrane produces a different feel than current implant membranes. These properties may be utilized to the advantage of various implant designs. In one preferred and non-limiting embodiment, the self-sealing nature of the membrane allows for adjustability without the need of special ports and filling valves. Some possible breast implant configurations will be described for purposes of summarizing this invention and making attributes of the membrane apparent as they relate to breast implant shells.

Therefore, in accordance with certain aspects of the invention and in one preferred and non-limiting embodiment, provided is an adjustable implant for volumetrically altering, replacing, expanding, or augmenting tissues. The implant includes an elastomeric, preferably self-sealing, membrane enclosed or partially enclosed about a main chamber. The implant is adapted to expand when filled with a fluid. The membrane includes an outer zone formed from at least one outer elastomeric layer; an inner zone formed from at least one inner elastomeric layer; and a middle zone formed from at least one elastomeric middle layer positioned between a least a portion of the outer zone and at least a portion of the inner zone. The implant is configured such that the middle zone is under contraction from a contracting force provided by the outer zone or the inner zone.

According to a further aspect of the invention and in another preferred and non-limiting embodiment, provided is a method of forming a fluid-filled adjustable implant for volumetrically altering, replacing, expanding, or augmenting tissues. The method includes forming a first zone of an elastomeric membrane defining at least one partially enclosed void space. The first zone includes at least one elastomeric layer. The method further includes: expanding a volume of the void space, thereby expanding the first zone; forming a second zone including one or more elastomeric middle layers on the first zone; reducing the volume of the void space, thereby contracting the first zone and the second zone; and forming a third zone including at least one elastomeric layer on the second zone. Thus, an elastomeric membrane including a first zone, a second zone, and a third zone is formed. The method further includes the step of forming an adjustable implant from the elastomeric membrane by enclosing the void space to form at least one chamber.

These and other features and characteristics of the present invention, as well as the methods of use and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

BRIEF DESCRIPTION OF THE DRAWINGS

Some of the advantages and features of the preferred embodiments of the invention have been summarized herein above. These embodiments along with other potential embodiments of the device will become apparent to those skilled in the art when referencing the following drawings in conjunction with the detailed descriptions as they relate to the figures.

FIG. 6 is a cross-sectional view of a casting mandrel for forming an elastomeric membrane of an adjustable implant, according to the principles of the invention;

FIG. 7 is a cross-sectional view of a portion of an elastomeric membrane formed from the mandrel of FIG. 6, during a subsequent processing step, according to the principles of the invention;

FIG. 8 is a cross-sectional view of a portion of the elastomeric membrane of FIG. 7, during a subsequent processing step, according to the principles of the invention;

FIG. 9 is an adjustable implant formed from the elastomeric membrane of FIG. 8, according to the principles of the invention;

FIG. 10 is a cross-sectional view of a casting mandrel for forming an elastomeric membrane of an adjustable implant, according to the principles of the invention;

FIG. 11 is a cross-sectional view of a portion of an elastomeric membrane formed from the mandrel of FIG. 10, during a subsequent processing step, according to the principles of the invention;

FIG. 12 is a cross-sectional view of a portion of the elastomeric membrane of FIG. 11, during a subsequent processing step, according to the principles of the invention;

FIG. 13 is an adjustable implant formed from the elastomeric membrane of FIG. 12, according to the principles of the invention;

FIG. 14 is a cross-sectional view of an elastomeric membrane for an adjustable implant, according to the principles of the invention;

FIG. 15 is a cross-sectional view of the elastomeric membrane of FIG. 14 in an inverted position, according to the principles of the invention;

FIG. 16 is a cross-sectional view of an adjustable implant formed from the elastomeric membrane of FIG. 14, according to the principles of the invention;

FIG. 17 is a cross-sectional view of a casting mold for forming an elastomeric membrane, according to the principles of the invention;

FIG. 18 is a cross-sectional view of a portion of an elastomeric membrane formed from the mold of FIG. 17, according to the principles of the invention;

FIG. 19 is a cross-sectional view of an apparatus for secondary casting for forming additional elastomeric layers on the portion of the elastomeric membrane of FIG. 18, according to the principles of the invention;

FIG. 20 is a cross-sectional view of a processing step for forming an elastomeric membrane from the portion of the membrane of FIG. 18 contained within the apparatus of FIG. 19, according to the principles of the invention;

FIG. 21 is a cross-sectional view of a processing step for forming an elastomeric membrane from the portion of the membrane of FIG. 18 contained within the apparatus of FIG. 19, according to the principles of the invention; and FIG. 22 is a cross-sectional view of an adjustable implant formed from the elastomeric membrane of FIG. 21, according to the principles of the invention.

DESCRIPTION OF THE INVENTION

Figure 1:
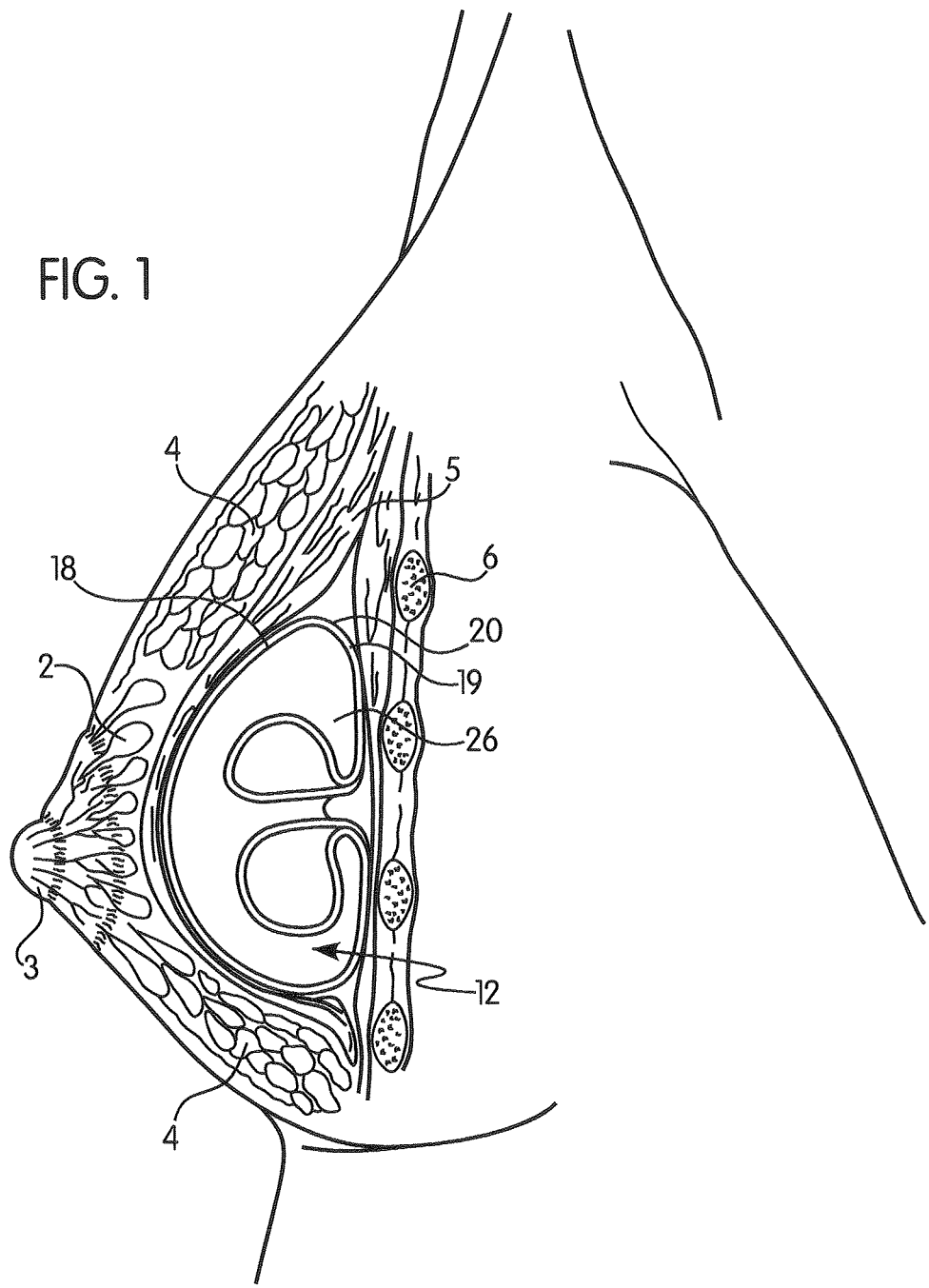
FIG. 1 is a sagittal view of a female human body through the left breast showing anatomical detail along with in situ placement of an adjustable implant, according to the principles of the invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

With reference to FIG. 1, a sectional view of an implant 12 placed within the left female human breast is illustrated. The implant 12, according to a preferred and non-limiting embodiment of the invention, is in a sub-muscular anatomical position under the pectoralis chest muscle 5. Alternatively, the implant can be positioned sub-muscularly or in sub-glandular placement. There are variations on these placements, but these two categories of placement are the most common practice. The sectional view of FIG. 1 provides basic anatomical landmarks for clarity. The implant 12 is posteriorly positioned against the chest wall tissues and underlying ribs 6. Anteriorly, the implant 12 may be positioned under the chest muscle tissue 5 with the greatest muscular coverage enveloping the superior anterior aspects of the implant 12. Anterior to the muscle tissues 5 are the intact subcutaneous fat 4 and mammary glands 2. The nipple 3 is the most anterior structure to the implant 12.

The implant 12 consists of multiple layers of an elastomeric membrane, also referred to as a shell. Generally, there are several high-performance silicone elastomer layers for enhanced shell integrity. Variable elastomers are utilized to provide a membrane with self-sealing properties. Although the membrane may include numerous layers, the layers may be generally classified in three zones or regions, namely, an inner zone 18, a middle zone 19, and an outer zone 20.

The inner zone 18 has one or more elastomeric layers that are strong and highly resistant to permeability. The layers of the inner zone 18 remain elastomeric and have significant ability to stretch and return to their original shape. These inner zone 18 layers are cured and set to a desired volume and shape, which encapsulates at least one chamber, such as outer chamber 26, of the implant 12.

The middle zone 19 consists of multiple layers of softer elastomeric material to envelop the inner zone 18 layers in a significantly expanded state. The middle zone 19 may be thicker than the inner zone 18 or the outer zone 20. During formation of the membrane, the inner zone 18 is expanded to allow for the larger volumetric form to be established. Once the middle zone 19 is cured, the inner zone 18 and the middle zone 19 are retracted to a volume and shape representative of the inner zone 18 in its original cured shape. Thus, the softer middle zone 19 is in significant contraction as it is forced to conform to a lesser volume. The outer zone 20 layers are then formed to envelope the middle zone 19 layers. The outer zone 20 has similar or identical properties to the inner zone 18 layers, being elastomeric, yet strong and resistant.

The resultant membrane consists of a middle zone 19 that is thicker and formed from softer elastomeric membrane, under contraction. The middle zone 19 is sandwiched between the inner zone 18 and the outer zone 20 of stronger and more stable elastomeric compounds. The resultant membrane has a total thickness of about 0.75 mm to 2.25 mm, and more preferably between about 1.0 mm and 1.25 mm. However, for certain applications, the membranes may have a total thickness below 0.75 millimeters or total thickness in excess of 2.25 millimeters. Furthermore, the membrane may be different thicknesses at different areas of the implant 12.

The three-zone configuration facilitates the self-sealing capability of the membrane. However, the design and configuration of the membrane is not limited to the three-zone configuration. Other arrangements of elastomeric layers may also be employed to provide the self-sealing ability of the membrane. Furthermore, as will be appreciated by one having ordinary skill in the art, manipulation of these zone layers and their configuration will produce further advantages of this invention. For example, multiple layers under contraction will increase the integrity and self-sealing potential of the membrane. Thickness of the layers under contraction also relates directly to integrity of the membrane. Therefore, a balance between the optimal number of layers and layer thickness should be established for particular applications.

The three-zone membrane can be punctured with a non-coring needle to access one or more chambers enclosed by the membrane. Non-coring needles are used to puncture the membrane without removing any of the silicone material forming the membrane layers. The geometry of a non-coring needle spreads and expands the silicon at the entry site. Upon retraction of the needle from the membrane, the silicone self-seals at the penetration site. The silicone must be under contractive forces to self-seal. This contraction is achieved by retaining the silicone membrane under mechanical compression from other elastomeric layers.

The self-sealing properties of the membrane produces an implant shell exhibiting properties different from existing implants. The compression of the middle zone 19 changes how the inflation forces are manifested in terms of the general feel of the implant 12. More specifically, the implant 12 can be varied in design to produce a more natural feel with less of an inflated or balloon characteristic. Furthermore, the properties of the membrane introduce a favorable variable that can be incorporated in various single or multiple chamber designs. For example, it is possible to alter the characteristics of the membrane to produce a saline-filled implant with more silicon-like characteristics.

It may be preferred to fill the chamber with biocompatible fillers, such as saline or saline with biocompatible thickening agents, so that in the event of leaking, the saline is naturally absorbed. Thickening agents can be designed to provide additional sealing ability from within the implant. Methycellulose has a high molecular mass and can be added to the saline to give it gel-like properties. Aqueous carboxymethylcellulose has proven biocompatibility and is utilized in some cosmetic filling agents. Polyethylene glycol (PEG) and saline would also be a suitable combination with thickening characteristics. The high molecular mass of PEG and other similar thickening agents will reduce the risk of leakage from the membrane. Furthermore, membranes of breast implants are generally made as thin as possible to achieve a softer feel. Thinner membranes impose greater risks with respect to puncture, capsular contraction, and gel or fluid bleeds. The three-zone shell inherently allows for slightly thicker and safer designs.

Having generally discussed the structure of the elastomeric membrane and fluid-filled adjustable implant, methods of manufacture of membranes and implants will now be described in detail. Additionally, further embodiments of an implant formed from an elastomeric membrane are also discussed. As will be appreciated by one of ordinary skill in the art, the manufacturing possibilities of this invention are extensive with respect to methods and materials. Drip casting around a mandrel is the traditional method of forming the primary shell of a breast implant. The reverse process of drip casting into a mold cavity can be an effective alternate approach. To illustrate the alternate manufacturing steps, preferred manufacturing processes using both casting methods are discussed herein. FIG. 2 through FIG. 16 are all based on forming viscoelastic membranes around mandrels. FIG. 17 through FIG. 22 illustrate forming viscoelastic membranes by means of molding.

With reference to FIGS. 2-16, methods of forming an elastomeric membrane by drip casting about a mandrel 17 are discussed herein. Generally, the inner zone 18 layers are formed on the mandrel 17. The mandrel 17 is then wasted, collapsed, or removed from the formed layers. There are many potential materials that can be utilized to form the mandrel 17. Gypsum plaster is a good example; however, various plastics could be employed as well. A plastic mandrel can be mechanically collapsed, softened with solvents, or heated to aid in removal without damaging the silicone castings. Gelatinous substances are another option that can provide sufficient stability to expand a membrane and form a mandrel that can be wasted and removed. Agar or agar-agar is one such form of a polysaccharide that can be molded into firm stable shapes. The possibilities for casting are extensive and different techniques may be employed for various applications of this invention.

An expansion medium 22 is utilized to expand the formed layers during later steps of the casting process. Such a medium 22 is necessary to retain a previously cast membrane in a desired expanded state, as well as to support a membrane volume in a retracted state. The expansion medium 22 has many possible choices of materials and techniques of employment. Gasses and fluids under pressure are the simplest mediums that can be used. Agar and other materials that can be poured and cast to a fixed volume and shape can also be utilized. Agar has a low melting point, which allows it to be liquefied for removal or recast as required. Beads are another option that can produce fixed volumes of variable shapes. The advantages and disadvantages of various expansion mediums will be apparent based on the requirements of the particular stage of manufacture.

Figure 2:
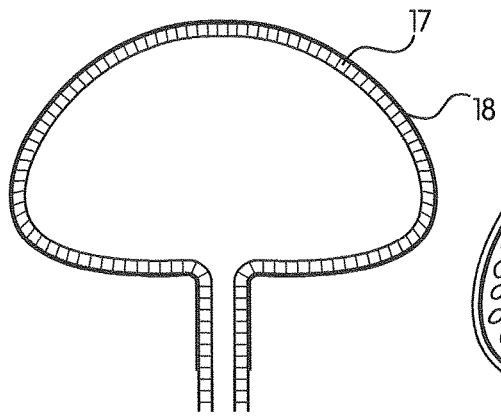
FIG. 2 is a cross-sectional view of a casting mandrel for forming an elastomeric membrane of an adjustable implant, according to the principles of the invention.

With reference to FIGS. 2-6, a method of forming a preferred and non-limiting embodiment of an implant 10 by drip casting about a mandrel 17 is provided. FIG. 2 is a sectional view of the drip casting mandrel 17. The mandrel 17 is formed from a material that will be destroyed after the inner zone 18 layers are cast. Thus, the mandrel 17 can be described as a waste drip casting mandrel. The mandrel 17 can be cast in gypsum plaster. The gypsum plaster is a viable option, as it can be cast very thin and can be easily removed by mechanical means and/or dissolved with sodium bicarbonate and water. Multiple elastomeric layers are drip cast onto the mandrel 17 to form the inner zone 18 of the membrane. The inner zone 18 viscoelastic layers must be very durable, essentially impermeable, exhibit stable memory characteristics, and still remain very elastic.

Figure 3:
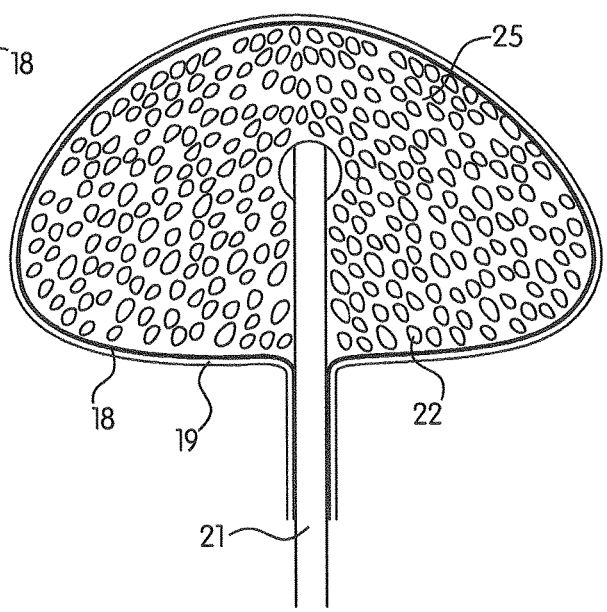
FIG. 3 is a cross-sectional view of a portion of an elastomeric membrane formed from the mandrel of FIG. 2, during a subsequent processing step, according to the principles of the invention.

In FIG. 3, the mandrel 17 has been wasted and the inner zone 18 shell has been filled with expansion medium 22 through a filling tube 21 for the purpose of expanding the shell to a desired volume. The expansion medium 22 is required to be a stable medium that can be altered in volume. The filling tube 21 has three functions. It inflates the inner shell 18, allowing the expansion medium 22 to pass through it and fill the expanded volume. Once the desired form is achieved, the filling tube 21 becomes a supporting handle, which creates a drip casting mandrel to apply the middle zone 19 viscoelastic layers. The middle zone 19 layers are applied directly on top of the inner zone 18. The middle zone 19 layers have a tacky, but cured state, which remains soft and elastic. Such pliable characteristics allow these layers to be put in a state of compression.

Figure 4:
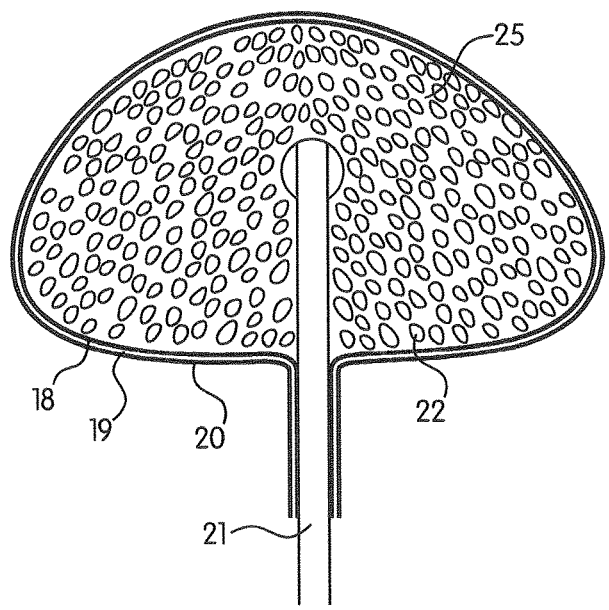
FIG. 4 is a cross-sectional view of a portion of the elastomeric membrane of FIG. 3, during a subsequent processing step, according to the principles of the invention.

FIG. 4 illustrates the third drip casting state. In this form, a portion of the expansion medium 22 has been removed to return the membrane to a volume and shape representative of the original mandrel 17. The filling tube 21 is utilized to create a vacuum retracting the inner zone layers and compressing the middle zone layers 19 to conform thereto. The outer zone 20 layers are drip cast to encase the middle 19 and inner zone 18 layers. The three-zone shell is complete when the outer zone 20 layers are cured. These outer zone 20 viscoelastic layers must be very durable, essentially impermeable, exhibit stable memory characteristics, and still remain very elastic. The layers of the outer zone 20 are essentially the same as, or similar to, the inner zone 18 viscoelastic layers.

Figure 5:
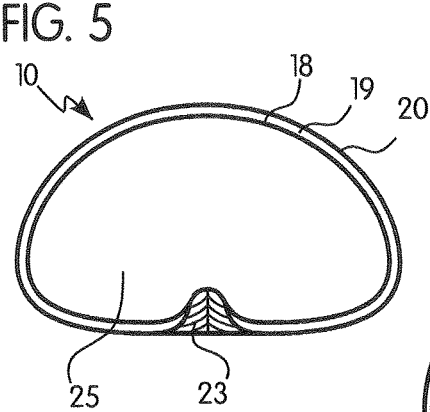
FIG. 5 is an adjustable implant formed from the elastomeric membrane of FIG. 4, according to the principles of the invention.

FIG. 5 illustrates a non-limiting and preferred embodiment of the implant 10 formed from a three-zone membrane in its completed state. To produce the implant 10, the expansion medium 22 is removed producing a void shell. The shell is cleaned and surplus membrane, formed along the filling tube 21, is trimmed away. The flange remaining around the hole that remains in the middle of the posterior aspect of the implant is inverted inward and a plug 23 is vulcanized to seal the implant 10. The plug 23 is formed from a viscoelastic material, similar to the material that forms the middle zone 19. The plug 23 functions as a self-sealing injection port that can be utilized to pre-fill a main chamber 25 of the implant 10 enclosed by the membrane to a desired volume prior to implantation. This plug 23 may take a variety of forms and configurations, such as a one-way valve, a flapper valve, an elastic valve, and the like. Further, the plug 23 may include one or more apertures or conduits through which to insert specified fluids into various areas of the implant 12. Biocompatible thickening agents can also be pre-filled prior to sealing the implant 10. The implant 10 is filled or partially filled with a fluid, such as saline, prior to implantation to a patient.

With reference to FIGS. 6-9, a method of manufacture is illustrated for the implant 12 depicted in FIG. 1. FIG. 6 is sectional view of a dual-chamber drip casting mandrel 17 used to form the inner zone 18 of the implant 12. The mandrel 17 is formed to a desired shape out of a material that will be destroyed after the inner zone 18 layers are cast to its form. The mandrel 17 can be described as a waste drip casting mandrel. The mandrel 17 can be cast in gypsum plaster. The gypsum plaster can be cast very thin and can be easily removed by mechanical means and/or dissolved with sodium bicarbonate and water. Multiple elastomeric layers are formed on the mandrel 17 to form the inner zone 18. The inner zone 18 viscoelastic layers must be very durable, essentially impermeable, exhibit stable memory characteristics, and still remain very elastic.

In FIG. 7, the dual chamber mandrel 17 has been wasted and both chambers of the inner zone 18 shell have been filled with the expansion medium 22 for the purpose of expanding the shell and retaining it to a desired volume. The filling tube 21 has three functions. It inflates the inner shell allowing the expansion medium 22 to fill the expanded volume. Once the desired form is achieved, the filling tube 21 becomes a supporting handle creating a drip casting mandrel to apply the middle zone 19 viscoelastic layers. The middle zone 19 layers are formed directly on the inner zone 18 and cured. The middle zone 19 layers are required to attain a tacky, but cured state, which remains soft and elastic. As in the previously described embodiment, the pliable layers are capable of being put in a compression state.

FIG. 8 illustrates the third drip casting state. In this form, a portion of the expansion medium 22 is removed to return the membrane to a volume and shape representative of the original mandrel 17. The filling tube 21 is utilized to create a vacuum retracting the inner zone 18 layers and compressing the middle zone 19 layers to conform thereto. The outer zone layers 20 are drip cast to encase the middle 19 and inner zone 18 layers. The three-zone membrane is completed when the outer zone 20 layers are cured. These outer zone 20 viscoelastic layers must be very durable, essentially impermeable, exhibit stable memory characteristics and still remain very elastic. Thus, they are essentially the same as or similar to the inner zone 18 viscoelastic layers.

FIG. 9 illustrates a preferred and non-limiting embodiment of the implant 12 in a completed state, formed from the elastomeric membrane depicted in FIGS. 7 and 8. To form the implant 12, the expansion medium 22 is removed producing a void shell. The shell is cleaned by appropriate measures. After cleaning, a smaller inner chamber 27 of the membrane is folded into an outer chamber 26 forming an implant in which the outer chamber 26 encloses the inner chamber 27. Thus, the inner chamber 27 membrane is inverted in its final position. A portion of the continuous membrane formed along the filling tube 21 becomes the termination of the membrane. As this portion of the membrane exits the posterior aspect the implant 12, surplus is trimmed away. Next, a plug 23 is vulcanized to seal the implant 12. The plug 23 is formed from viscoelastic material similar to the middle zone 19. The plug 23 functions as a self-sealing injection port that can be utilized to pre-fill the outer chamber 26 and inner chamber 27 of the implant to a desired volume prior to implantation. Biocompatible thickening agents can also be pre-filled prior to sealing the implant. In this final configuration, the implant 12 has a continuous viscoelastic membrane forming two self-sealing independent chambers. The implant 12 is filled or partially filled with a fluid, such as saline, prior to implantation to a patient.

With reference to FIGS. 10-13, a method of manufacture of a further embodiment of an adjustable implant 13 is illustrated. More specifically, FIG. 10 is sectional view of a three-chamber drip casting mandrel 17 used for the initial forming of implant 13, according to a preferred and non-limiting embodiment of the invention. The mandrel 17 is formed to a desired shape out of a material that will be destroyed after the inner zone 18 layers are cast to its form. The mandrel 17 can be described as a waste drip casting mandrel 17. The mandrel 17 can be cast in gypsum plaster. The gypsum plaster can be cast very thin and can be easily removed by mechanical means and/or dissolved with sodium bicarbonate and water. Multiple elastomeric layers are drip cast to the mandrel 17 to form the inner zone 18. The inner zone 18 viscoelastic layers must be very durable, essentially impermeable, exhibit stable memory characteristics, and still remain very elastic.

In FIG. 11, the three-chamber mandrel 17 is wasted and the main chamber of the inner zone 18 shell is filled with the expansion medium 22 for the purpose of expanding the shell and retaining it to a desired volume. The filling tube 21 requires a retaining clip 24 to seal the neck to the outer chamber 26 and also pull the two smaller chambers (collectively inner chamber 27) away from the outer chamber 26. The filling tube 21 has three functions. It inflates the inner zone 18 shell of the outer chamber 26 allowing the expansion medium 22 to pass through it and fill the expanded volume. Once the desired form is achieved, the filling tube 21 becomes a supporting handle creating a drip casting mandrel. The middle zone 19 viscoelastic layers are applied directly to portions of the inner zone 18. In a preferred and non-limiting embodiment, the middle zone 19 viscoelastic layer is only drip cast on the outer chamber 26. The middle zone 19 layers are required to attain a tacky, but cured state which remains soft and elastic. These pliable characteristics mean that the middle zone 19 layers can be placed in a state of compression.

FIG. 12 illustrates the third drip casting state. In this form, a portion of the expansion medium 22 is removed to return the outer chamber 26 to a volume and shape representative of the original mandrel 17. The expansion medium 22 is also added to the inner chambers 27 to fill them to a volume and shape representative of the original mandrel 17. The filling tube 21 is utilized to create a vacuum pressure, thereby retracting the entire structure and compressing the middle zone 19 layers to conform thereto. The outer zone 20 layers are drip cast to encase the middle zone 19 and inner zone 18 layers. The three-chamber shell is complete when the outer zone 20 layers are cured. These outer zone 20 viscoelastic layers must be very durable, essentially impermeable, exhibit stable memory characteristics, and still remain very elastic. They are essentially the same as or similar to the inner zone 18 viscoelastic layers. The final three-chamber shell consists of an outer chamber 26 shell which has the three layer self-sealing properties. The two smaller chambers (collectively inner chambers 27) only include inner zone 18 and outer zone 20 layers.

FIG. 13 illustrates a preferred embodiment of the implant 13, formed from the membrane layers of FIGS. 11 and 12, in its completed state. The expansion medium 22 is removed, producing a void shell. The shell is cleaned through appropriate measures. The two smaller chambers (collectively inner chambers 27) are folded into the outer chamber 26. Thus, the inner chamber 27 membrane has an inverted outer aspect and non-inverted inner aspect in its final position. A portion of the continuous membrane along the filling tube 21 forms the ends of the membrane. A port for accessing the outer chamber 26 of the membrane is positioned at the ends of the membrane. Surplus material is trimmed from this portion of the membrane. A plug 23 is vulcanized to seal the implant 13 in the port. The plug 23 is to be formed from viscoelastic material similar to the middle zone 19. The plug 23 functions as a self-sealing injection port that can be utilized to pre-fill the outer chamber 26 and inner chamber 27 of the implant 13 to a desired volume prior to implantation. Biocompatible thickening agents can also be pre-filled prior to sealing the implant. It is noted that the inner chamber 27 may be perforated to allow fluid communication of all chambers. This configuration utilizes the inner structures to provide baffling characteristics to calm fluid motion of the liquid utilized to fill the chambers. The implant 13 is filled or partially filled with a fluid, such as saline, prior to implantation to a patient.

With reference to FIGS. 14-16, a method of forming a further preferred and non-limiting embodiment of an adjustable implant 14 is illustrated. FIG. 14 depicts a completed shell formed by drip casting around a mandrel, including inner zone layers 18, middle layers 19, and outer zone layers 20. The completed shell is similar in shape to completed shells illustrated in FIG. 6 and FIG. 7. In FIG. 14, the expansion medium 22 was removed producing a void shell. The shell was also cleaned after the expansion medium 22 was removed. The shell is inflated enough to maintain its shape and a temporary plug 30 is positioned near an opening of the shell. Viscoelastic tendrils 29 are formed or vulcanized on one of the chambers of the shell.

FIG. 15 depicts the next formation stage, where the entire membrane is inverted upon itself, such that tendrils 29 extend inward into the inner chamber 27. The final configuration of the implant 14 with tendrils 29 is illustrated in FIG. 16. The smaller inner chamber 27 with tendrils 29 is folded into the outer chamber 26. The inner chamber 27 is not inverted in its final position. The tendrils 29 expand into the outer chamber 26 providing stability to the final form and baffling characteristics to calm fluid motion in the outer chamber 26. The outer chamber 26 membrane remains inverted in its final position. A portion of the continuous membrane formed along the filling tube 21 forms the termination of the membrane. As this portion of the membrane exits the posterior aspect of the implant 13, the surplus membrane material is trimmed. A plug 23 is vulcanized to seal the implant 14. The plug 23 is to be formed from viscoelastic material similar to the middle zone 19. The plug 23 functions as a self-sealing injection port that can be utilized to pre-fill the outer chamber 26 and inner chamber 27 of the implant 14 to a desired volume prior to implantation. Biocompatible thickening agents can also be pre-filled prior to sealing the implant. This final configuration of the implant 14 has a continuous viscoelastic membrane forming two self-sealing independent chambers, namely outer chamber 26 and inner chamber 27. The implant 14 is filled or partially filled with a fluid, such as saline, prior to implantation to a patient.

With reference to FIGS. 17-22, a method of manufacturing an implant 11 is depicted. Unlike previously described embodiments of the invention, the implant 11 is manufactured by drip casting into a mold cavity. The process is essentially the reverse from previous examples and uses a molding method to form the various layers in molding cavities instead of externally around drip casting mandrels. The layers are cast and cured in the reverse order, starting with the layers of the outer zone 20. FIG. 17 illustrates a mold utilized to produce the viscoelastic layers of the outer zone 20, which are very durable, essentially impermeable, exhibit stable memory characteristics, and still remain very elastic. In this casting process, the mold 17b is reusable and may be made from glass or rigid plastic. A clear material is generally preferable, allowing for visual inspection during the casting process. Various methods of casting may be employed from simple manual techniques to mechanical spin casting. The purpose of this initial stage is to produce a complete form of the viscoelastic layers of the outer zone 20 as seen in FIG. 18. This outer shell may alternately be produced by means of drip casting upon a mandrel. Regardless of the method, the viscoelastic layers of the outer zone 20 are cured to the required shape and provide the base upon which the remaining layers are laminated. FIG. 18 illustrates a void shell of the outer zone 20 layers.

FIG. 19 illustrates the apparatus required to cast the remaining layers. The outer body of the apparatus 33 is rigid with an evacuation valve 34 and an internal bladder 17c. The purpose of this apparatus is to create an internal mold cavity that can be expanded and retracted through the laminating process. The bladder 17c has a base shape reflective of the final form of the preferred and non-limiting embodiment of the implant illustrated in FIG. 5. The bladder 17c has elastic properties and strong memory of form. It will require perforations to allow communication between the mold cavity and evacuation chamber 35 created by the outer body of the apparatus 33. In FIG. 19, the previously formed outer zone 20 viscoelastic layers are positioned within the bladder 17c and retracted to conform to the matching shape of the mold cavity created by the bladder 17c. A slight vacuum pressure is required to hold the outer zone 20 layers in place. The bladder 17c and outer zone 20 layers are sealed around a collar of the apparatus 33 body. The vacuum pressure is maintained by utilizing the evacuating valve 34. In certain embodiments, the contact surface between the bladder 17c and the viscoelastic layers of the outer zone 20 requires lubrication to equalize and marry the conforming shapes. Once positioned and retained, the apparatus 33 is configured to expand the bladder 17c along with the outer zone 20 viscoelastic layers to a desired size and shape.

In FIG. 20, the complex of the bladder 17c and the previously formed outer zone 20 layers are expanded and retained in an expanded form by closing the evacuation valve 34 to seal the evacuation chamber 35. The expanded mold cavity is ready to laminate the middle zone 19 layers. The middle zone 19 layers are required to attain a tacky, but cured state which remains soft and elastic. These middle zone 19 layers may have pliable characteristics that allow the layers to be placed in a state of compression. The middle zone 19 layers are cast in one or more layers by manual or mechanical means, similar to the previously cast outer zone 20 layers. After casting of the middle zone 19 layers is complete, the layers are subjected to compression by opening the evacuation valve 34. This allows the bladder 17c to return to its original memory shape with the laminated outer zone 20 layers and middle zone 19 layers. The process of retraction may be done in a cured or partially cured state to allow manipulation of desired characteristics of the membrane complex.

In FIG. 21, the apparatus is configured in a final molding state. The outer zone 20 and middle zone 19 laminated membranes are retracted to a shape representative of the final form of the embodiment of the implant 10 depicted in FIG. 5. Adequate vacuum pressure remains in the evacuation chamber 35 to stabilize the form for molding. The inner zone 18 viscoelastic layers are cast in one or more layers by manual or mechanical means, similar to the previously cast layers. These inner zone 18 layers must be very durable, essentially impermeable, exhibit stable memory characteristics, and still remain very elastic. Once the inner zone 18 layers are cured, the three-zone membrane is complete and ready for removal. The vacuum is released and the laminated implant shell is pulled through the collar of the apparatus 33 neck.

FIG. 22 illustrates the implant 11 in a completed state. The implant 11 is essentially identical to the implant 10 illustrated in FIG. 5. To produce the completed implant 11, the void is cleaned by appropriate measures and surplus membrane that formed along the apparatus 33 collar is trimmed.

The flange remaining around the hole that remains in the middle of the posterior aspect of the implant 11 is inverted inward and a plug 23 is vulcanized to seal the implant. The plug 23 is formed from viscoelastic material similar to the middle zone 19. The plug 23 functions as a self-sealing injection port that can be utilized to pre-fill the main chamber 25 of the implant to a desired volume prior to implantation. Biocompatible thickening agents can also be pre-filled prior to sealing the implant. The implant 11 is filled or partially filled with a fluid, such as saline, prior to implantation to the patient.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements. For example, it is to be understood that the present invention contemplates that, to the extent possible, one or more features of any embodiment can be combined with one or more features of any other embodiment.

The invention claimed is:

1. A method of forming a fluid-filled implant, comprising:
   forming a first zone of an elastomeric membrane defining at least one partially enclosed void space, the first zone comprising at least one elastomeric layer;
   expanding a volume of the at least one partially enclosed void space, thereby expanding a volume enclosed by the first zone;
   forming a second zone comprising at least one elastomeric layer on at least a portion of the expanded first zone;
   reducing the volume of the at least one partially enclosed void space, thereby contracting the elastomeric layers of the first zone and the second zone; and
   forming the adjustable implant from the elastomeric membrane by enclosing the at least one partially enclosed void space to form at least one chamber.

2. The method of claim 1, further comprising forming a third zone after reducing the volume of the at least one partially enclosed void space, the third zone comprising at least one elastomeric layer on at least a portion of the second zone, thereby providing an elastomeric membrane comprising a first zone, a second zone, and a third zone.

3. The method of claim 2, wherein forming the second zone comprises curing the at least one elastomeric middle layer of the second zone to a state that is softer than the elastomeric layers of the first zone and the third zone.

4. The method of claim 1, wherein a volume enclosed by the second zone at the time of forming is larger than a volume enclosed by the first zone at the time of forming, resulting in compression of the second zone by the first zone.

5. The method of claim 1, wherein at least one of the first zone and the second zone is formed by casting into a mold.

6. The method of claim 5, wherein forming the first zone comprises introducing elastomeric material into the mold and curing the material to form the at least one elastomeric layer.

7. The method of claim 6, wherein an outer surface of the at least one elastomeric layer of the first zone substantially conforms to an inner surface of the mold.

8. The method of claim 5, wherein expanding the volume of the at least one partially enclosed void space, thereby expanding the volume enclosed by the first zone, comprises modifying an exterior pressure applied to the first zone.

9. The method of claim 8, wherein the exterior pressure is modified by an evacuation chamber.

10. The method of claim 8, wherein forming the second zone comprises providing an elastomeric material to an inner surface of the expanded first zone and curing the material, thereby forming the at least one elastomeric layer of the second zone.

11. The method of claim 8, wherein reducing the volume of the at least one partially enclosed void space comprises modifying the exterior pressure, thereby contracting the first zone and the second zone.

12. The method of claim 5, further comprising, after reducing the volume of the at least one partially enclosed void space, forming a third zone by casting an elastomeric material onto the second zone, the third zone comprising at least one elastomeric layer on at least a portion of the second zone.

13. The method of claim 12, wherein the at least one elastomeric layer of the third zone is a continuous layer extending into an opening of the at least one partially enclosed void space defined by the first zone and the second zone, thereby forming the enclosed chamber.

14. The method of claim 1, wherein forming the implant by enclosing the at least one partially enclosed void space comprises vulcanizing a plug in an opening of the at least one partially enclosed void space, thereby forming the chamber.

15. The method of claim 1, further comprising filling or partially filling the chamber with a biocompatible fluid or gel to form the implant.

16. The method of claim 15, wherein the biocompatible fluid comprises saline.

17. The method of claim 1, wherein a volume of the chamber of the implant is about 80 cc to 800 cc.

18. The method of claim 1, wherein a total thickness of the elastomeric membrane is at least 2.25 mm.

19. The method of claim 1, wherein at least one of the first zone and the second zone is formed by drip casting over a mandrel.

20. The method of claim 19, wherein expanding the at least one partially enclosed void space comprises filling the at least one partially enclosed void space with an expansion medium, thereby increasing the volume enclosed by the first zone.

* * * * *